(12) United States Patent
Yang et al.

(10) Patent No.: US 11,718,880 B2
(45) Date of Patent: Aug. 8, 2023

(54) MARKER AND DIAGNOSIS METHOD FOR NONINVASIVE DIAGNOSIS OF MYOCARDIAL INFARCTION

(71) Applicant: BEIJING MEDINTELL BIOMED CO., LTD, Beijing (CN)

(72) Inventors: Chenggang Yang, Beijing (CN); Shuguang Li, Beijing (CN)

(73) Assignee: BEIJING MEDINTELL BIOMED CO., LTD, Beijing (CN)

( * ) Notice: Subject to any disclaimer, the term of this patent is extended or adjusted under 35 U.S.C. 154(b) by 135 days.

(21) Appl. No.: 17/247,534

(22) Filed: Dec. 15, 2020

(65) Prior Publication Data

US 2021/0115516 A1    Apr. 22, 2021

Related U.S. Application Data

(63) Continuation-in-part of application No. PCT/CN2019/094268, filed on Jul. 1, 2019.

(30) Foreign Application Priority Data

| Jul. 3, 2018 | (CN) | 201810715884.7 |
| Jul. 3, 2018 | (CN) | 201810715888.5 |
| Jul. 3, 2018 | (CN) | 201810717258.1 |
| Jul. 3, 2018 | (CN) | 201810717286.3 |
| Jul. 3, 2018 | (CN) | 201810718258.3 |
| Jul. 3, 2018 | (CN) | 201810718260.0 |

(51) Int. Cl.
C12Q 1/68        (2018.01)
C12P 19/34       (2006.01)
C12Q 1/6883      (2018.01)

(52) U.S. Cl.
CPC ..... *C12Q 1/6883* (2013.01); *C12Q 2600/158* (2013.01)

(58) Field of Classification Search
CPC .......... C12Q 1/6883; C12Q 2600/158
See application file for complete search history.

(56) References Cited

FOREIGN PATENT DOCUMENTS

| CN | 105177171 A | 12/2015 |
| CN | 105349641 A | 2/2016 |
| CN | 105349642 A | 2/2016 |
| CN | 107164550 A | 9/2017 |
| CN | 107254537 A | 10/2017 |
| CN | 107312851 A | 11/2017 |
| CN | 107312852 A | 11/2017 |
| CN | 108004316 A | 5/2018 |
| CN | 105400880 B | 7/2018 |
| CN | 108624680 A | 10/2018 |
| CN | 108753956 A | 11/2018 |
| CN | 108753957 A | 11/2018 |
| CN | 108796067 A | 11/2018 |
| CN | 108796068 A | 11/2018 |
| CN | 108796069 A | 11/2018 |
| WO | 2012031008 A2 | 3/2012 |

OTHER PUBLICATIONS

Panagiota Kontou, et al. "Identification of gene expression profiles in myocardial infarction: a systematic review and meta-analysis" BMC Medical Genomics (2018) 11:109 (Year: 2018).*
Marc Ruel, et al. "Gene expression profile after cardiopulmonary bypass and cardioplegic arrest" The Journal of Thoracic and Cardiovascular Surgery, vol. 126, No. 5 (Year: 2003).*
Linlin Qiu, et al., "Identification of key genes involved in myocardial infarction" Eur J Med Res (2019) 24:22 (Year: 2019).*
Evan D. Muse, et al. "A Whole Blood Molecular Signature for Acute Myocardial Infarction" Scientific Reports vol. 7, Article No. 12268 (Published: Sep. 25, 2017) (Year: 2017).*
Marek Kiliszek, et al. "Altered Gene Expression Pattern in Peripheral Blood Mononuclear Cells in Patients with Acute Myocardial Infarction" PLoS One. 2012;7(11):e50054. doi: 10.1371/journal.pone.0050054. Epub Nov. 21, 2012 (Year: 2012).*
Series GSE62646 from the Gene Expression Omnibus, https://www.ncbi.nlm.nih.gov/geo/query/acc.cgi?acc=GSE62646, Public on Oct. 23, 2014 (Year: 2014).*
Series GSE66360 from the Gene Expression Omnibus, https://www.ncbi.nlm.nih.gov/geo/query/acc.cgi?acc=GSE66360, Public on Feb. 28, 2015 (Year: 2015).*
J. Perren Cobb, et al. "Sepsis gene expression profiling: Murine splenic compared with hepatic responses determined by using complementary DNA microarrays" Crit Care Med 2002 vol. 30, No. 12 (Year: 2002).*
Vivian G. Cheung, et al. "Natural variation in human gene expression assessed in lymphoblastoid cells" Nature Genetics, vol. 33, Mar. 2003 Published online Feb. 3, 2003 (Year: 2003).*
Y. Hoshikawa, et al. "Hypoxia induces different genes in the lungs of rats compared with mice" Physiol Genomics 12: 209-219, 2003 (Year: 2003).*
Wong, K.L. et al. "Gene expression profiling reveals the defining features of the classical, intermediate, and nonclassical human monocyte subsets" Blood (2011) 118 (5): e16-e31. (Year: 2011).*

(Continued)

*Primary Examiner* — Stephen T Kapushoc
(74) *Attorney, Agent, or Firm* — NKL Law; Allen Xue (57) ABSTRACT

The present invention discloses a marker and a diagnosis method for the noninvasive diagnosis of myocardial infarction. According to the method disclosed by the present invention, second-generation sequencing and QPCR methods are used to find that there are significant differences in the expression of ING1, RAE1, DOCK10, KDSR, IVD, and MAEA in the blood of patients with myocardial infarction and normal subjects, that is, the expression of ING1, RAE1, DOCK10, KDSR, IVD and MAEA can be detected to determine whether the subjects suffer from myocardial infarction. According to the correlation between the two, the present invention develops a kit for the diagnosis of the myocardial infarction, and the kit is used for the diagnosis of the myocardial infarction by detecting the expression of ING1, RAE1, DOCK10, KDSR, IVD and MAEA. The diagnostic kit can be used for the early diagnosis of diseases, and has wide application prospect clinically.

3 Claims, 4 Drawing Sheets

Specification includes a Sequence Listing.

(56) References Cited

OTHER PUBLICATIONS

Alexandra-Chloe Villani, et al. "Single-cell RNA-seq reveals new typesof human blood dendritic cells,monocytes, and progenitors" Science 356.6335 (2017): eaah4573 (Year: 2017).*
Peter J. B. et al.; "Roles for Endoplasmic ReticulumAssociated Degradation and the Novel Endoplasmic Reticulum Stress Response Gene Derlin-3 in the Ischemic Heart", Circulation Research, vol. 106, Nov. 25, 2009, p. 308, right column, paragraph 3, p. 310, right column, the last paragraph to p. 311, left column, paragraph 1, and table VI.
Cheng, Ming et al.; "Identifying Key Genes Associated with Acute Myocardial Infarction" Medicine, vol. 96, No. 42, Dec. 31, 2017, the abstract, and p. 3, right column, paragraph 2.
Ross, J. JR. et al.; A 50-year research journey—From laboratory to clinic; Circulation journal: official journal of the Japanese Circulation Society, vol. 73, Jan. 2009; pp. 3-12.
Suresh, X. R. et al.; Transcriptome from circulating cells suggests dysregulated pathways associated with long-term recurrent events following first-time myocardial infarction; Journal of molecular and cellular cardiology, 74 (2014), pp. 13-21.
Ashburner, M. C. et al.; Gene Ontology: tool for the unification of biology; Nature Genetics, vol. 25, May 2000, pp. 25-29.

* cited by examiner

MARKER AND DIAGNOSIS METHOD FOR NONINVASIVE DIAGNOSIS OF MYOCARDIAL INFARCTION

CROSS REFERENCES TO RELATED APPLICATIONS

The present application is a continuation in part application of international application no. PCT/CN2019/094268, filed Jul. 1, 2019, which claims priority to Chinese Patent Application No. 201810718258.3, entitled "Diagnostic Marker-ING1 Gene of Myocardial Infarction"; Chinese Patent Application No. 201810715884.7, entitled "Use of RAE1 gene or protein as a biomarker for the diagnosis of myocardial infarction"; Chinese Patent Application No. 201810717286.3, entitled "DOCK10 gene for the early diagnosis of myocardial infarction"; Chinese Patent Application No. 201810715888.5, entitled "Use of KDSR gene in the preparation of myocardial infarction diagnostic tools"; Chinese Patent Application No. 201810718260.0, entitled "IVD gene for the diagnosis of myocardial infarction and use thereof"; and Chinese Patent Application No. 201810717258.1, entitled "New diagnostic function of MAEA gene in blood", filed in the Chinese Patent Office on Jul. 3, 2018, the entire contents of which are incorporated herein by reference.

INCORPORATION OF SEQUENCE LISTING

This application contains a sequence listing submitted in Computer Readable Form (CRF). The CFR file containing the sequence listing entitled "PA630-0001_ST25.txt", which was created on Dec. 15, 2020, and is 3,386 bytes in size. The information in the sequence listing is incorporated herein by reference in its entirety.

TECHNICAL FIELD

The present application belongs to the field of molecular diagnosis, and relates to a marker and a diagnosis method for the noninvasive diagnosis of myocardial infarction, in particular to use of blood markers ING1, RAE1, DOCK10, KDSR, IVD, MAEA in the diagnosis of myocardial infarction.

BACKGROUND

Myocardial infarction is a global public health problem that seriously threatens public health (J. Ross, Jr., A 50-year research journey. From laboratory to clinic, Circulation journal: official journal of the Japanese Circulation Society, 73 (2009) 3-12; D. Lloyd-Jones, R. Adams, M. Carnethon, G. De Simone, T. B. Ferguson, K. Flegal, E. Ford, K. Furie, A. Go, K. Greenlund, N. Haase, S. Hailpern, M. Ho, V. Howard, B. Kissela, S. Kittner, D. Lackland, L. Lisabeth, A. Marelli, M. McDermott, J. Meigs, D. Mozaffarian, G. Nichol, C. O'Donnell, V. Roger, W. Rosamond, R. Sacco, P Sorlie, R. Stafford, J. Steinberger, T. Thom, S. Wasserthiel-Smoller, N. Wong, J. Wylie-Rosett, Y. Hong, C. American Heart Association Statistics, S.). Several methodologies can be effectively applied to the treatment of myocardial infarction, such as percutaneous coronary intervention or coronary revascularization, which can protect locally necrotic myocardium through which blood flows and reduce the area of necrosis. Clinical results in patients with acute myocardial infarction after treatment showed improved left ventricular muscle infarction. However, the current treatment for acute myocardial infarction is still limited, mainly due to the very narrow time window of treatment (R. Suresh, X. Li, A. Chiriac, K. Goel, A. Terzic, C. Perez-Terzic, T J Nelson, transcriptome from circulating cells suggests dysregulated pathways associated with long-term recurrent events following first-time myocardial infarction, Journal of molecular and cellular cardiology, 74 (2014) 13-21.). Therefore, there is an urgent need to understand the main molecular mechanisms when acute myocardial infarction occurs.

Myocardial infarction is a complex physiological process, wherein ischemia leads to the cascade amplification of the expression of some genes in myocardial cells, and further causes the apoptosis or necrosis of the myocardial cells, thereby prolonging the treatment time window of the myocardial infarction, inhibiting the gene expression in downstream regions, and effectively preventing the apoptosis or necrosis of the myocardial cells (M. Ashburner, C. A. Ball, J. A. Blake, D. Botstein, H. Butler, J. M. Cherry, A. P. Davis, K. Dolinski, S. S. Dwight, J. T. Eppig, M. A. Harris, D. P. Hill, L. Issel-Tarver, A. Kasarskis, S. Lewis, J. C. Matese, J. E. Richardson, M. Ringwald, G. M. Rubin, G. Sherlock, Gene ontology: tool for the unification of biology. The Gene Ontology Consortium, Nature genetics, 25 (2000) 25-29). A new basis for basic research and clinical diagnosis can be provided by analyzing the genes of early response after myocardial ischemia, studying the gene expression profile of myocardial ischemia over time, and revealing the gene activity during myocardial ischemia. Various physiological processes (e.g. inflammation, abnormal calcium uptake, abnormal cell cycle, peptide secretion, oxidative stress, apoptosis, etc.) accompany the occurrence of myocardial infarction; at present, the precise time at which these processes occur and the time when some of the associated genes are expressed following myocardial ischemia are not known and need to be further explored. More and more studies have found that specific genes can be used as biomarkers for the diagnosis of myocardial infarction, as disclosed in the patent of the following application number: 201710592045.6, 201510923782.0, 201810019374.6, 201710592044.1, 201510727115.5, 201510727744.8, 201710591408.4, 201710592593.9, and 201510727102.8. As most diseases regulated by multiple genes, it is necessary to jointly diagnose a large number of genes in order to improve the diagnosis accuracy of the diseases, so that more molecular markers related to myocardial infarction need to be discovered for clinical application.

SUMMARY

To remedy the deficiencies of the prior art, it is an object of the present application to provide a marker and a diagnosis method for the noninvasive diagnosis of myocardial infarction. Compared with a traditional method for the diagnosis of myocardial infarction, the method for the diagnosis of myocardial infarction with gene markers has timeliness, specificity and sensitivity, so that patients can be aware of the risk of the disease in the early stage, and take corresponding preventive and therapeutic measures according to the risk.

To achieve the above objective, the present application adopts the following technical solutions.

The present application provides a marker for the diagnosis of the tendency of incidence of myocardial infarction, wherein the marker is selected from one or more of the following groups: ING1, RAE1, DOCK10, KDSR, IVD and MAEA.

The present application provides use of a reagent for detecting the expression of the marker in the preparation of a product for the diagnosis of myocardial infarction.

Further, the above-mentioned reagents for detecting the expression of the aforementioned markers comprise reagents for the diagnosis of myocardial infarction by detecting the expression level of the aforementioned markers through reverse transcription PCR, real-time quantitative PCR, immunoassay, in situ hybridization, chip or high throughput sequencing platform.

Further, the reagent for the diagnosis of myocardial infarction by detecting the expression level of the marker through reverse transcription PCR comprises at least a pair of primers for specifically amplifying the marker; the reagent for the diagnosis of myocardial infarction by detecting the expression level of the marker through real-time quantitative PCR comprises at least a pair of primers for specifically amplifying the marker; the reagent for the diagnosis of myocardial infarction by detecting the expression level of the marker through immunoassay comprises an antibody specifically binding to the marker; the reagent for the diagnosis of myocardial infarction by detecting the expression level of the marker through in situ hybridization comprises a probe hybridized with the nucleic acid sequence of the marker; the reagent for the diagnosis of myocardial infarction by detecting the expression level of the marker through a chip comprises a protein chip and a gene chip, wherein the protein chip comprises an antibody specifically binding to the marker, and the gene chip comprises a probe hybridized to the nucleic acid sequence of the marker.

In a specific embodiment of the present application, the reagent for the diagnosis of myocardial infarction by detecting the expression level of the marker through real-time quantitative PCR comprises at least one pair of primer sequences for specifically amplifying the marker as follows:
the primer sequences of ING1 are shown as SEQ ID NO.1 and SEQ ID NO.2;
the primer sequences of RAE1 are shown as SEQ ID NO.3 and SEQ ID NO.4;
the primer sequences of DOCK10 are shown as SEQ ID NO.5 and SEQ ID NO.6;
the primer sequences of KDSR are shown as SEQ ID NO.7 and SEQ ID NO.8;
the primer sequences of the IVD are shown as SEQ ID NO.9 and SEQ ID NO.10; and
the primer sequences of MAEA are shown in SEQ ID NO.11 and SEQ ID NO.12.

Preferably, the diagnostic product comprises a chip, a kit, test paper or a high throughput sequencing platform. The high-throughput sequencing platform is a special diagnostic product, and the reagent for detecting the expression of the marker can be applied to the platform to detect the expression of the marker. With the development of high-throughput sequencing technology, it is very convenient to construct personal gene expression profile. By comparing gene expression profiles between disease patients and normal populations, it is easy to analyze which gene abnormalities are associated with diseases. Therefore, knowing that the aforementioned abnormality of the marker is related to myocardial infarction in high-throughput sequencing also belongs to the use of the aforementioned marker, and is also within the protection scope of the present application.

The present application also provides a product for the diagnosis of myocardial infarction, which comprises a chip, a kit, test paper or a high-throughput sequencing platform.

Wherein, the chip comprises a gene chip and a protein chip; the gene chip comprises a solid phase carrier and oligonucleotide probes fixed on the solid phase carrier, wherein the oligonucleotide probes comprise a marker-targeted oligonucleotide probe for detecting the transcription level of the marker; the protein chip comprises a solid phase carrier and a specific antibody against the marker fixed on the solid phase carrier; the gene chip can be used for detecting the expression levels of a plurality of genes including the aforementioned markers, such as, a plurality of genes associated with myocardial infarction; the protein chip can be used for detecting the expression levels of a plurality of proteins including the aforementioned markers, such as a plurality of proteins associated with myocardial infarction. By simultaneously detecting multiple markers associated with myocardial infarction, the accuracy of diagnosis of myocardial infarction can be greatly improved.

Wherein, the kit comprises a gene detection kit including a reagent for detecting the transcription level of the aforementioned marker and a protein immunoassay kit including a specific antibody against the aforementioned marker. Further, the reagents comprise the reagents required in detecting the expression levels of the aforementioned markers using RT-PCR, real-time quantitative PCR, immunoassay, in situ hybridization, or chip methods. Preferably, the reagents comprise primers and/or probes for the aforementioned markers. Primers and probes that can be used to detect the expression levels of the aforementioned markers are readily designed based on the nucleotide sequence information of the aforementioned markers.

The probes that hybridize with the nucleic acid sequences of the aforementioned markers may be DNA, RNA, DNA-RNA chimeras, PNA or other derivatives. The length of the probe is not limited, as long as specific hybridization and specific binding to the nucleotide sequence of interest are accomplished, any length is acceptable. The probe may be as short as 25, 20, 15, 13 or 10 bases in length. Also, the probe may be as long as 60, 80, 100, 150, 300 base pairs or more in length, even the entire gene. Since different probe lengths, typically at least 14 base pairs in length and typically no more than 30 base pairs in length, have different effects on hybridization efficiency and signal specificity, the length complementary to the targeted nucleotide sequence is optimally between 15 and 25 base pairs. Preferably, the self-complementary sequence of the probe is less than 4 base pairs so as not to affect the hybridization efficiency.

The high throughput sequencing platform comprises reagents for detecting the expression levels of the aforementioned markers.

The test paper comprises a test paper carrier and an oligonucleotide fixed on the test paper carrier, wherein the oligonucleotide can detect the transcription level of the aforementioned marker.

Further, the specific antibodies against the aforementioned markers comprise monoclonal antibodies and polyclonal antibodies. The specific antibodies against the aforementioned markers comprise intact antibody molecules, any fragments or modifications of antibodies (e.g., chimeric antibodies, scFv, Fab, F (ab') 2, Fv, etc.), as long as the fragments can retain the ability of binding to the aforementioned markers. The preparation of antibodies for protein levels is well known to those skilled in the art, and any method may be used in the present application to prepare the antibodies.

In a specific embodiment of the present application, the primer sequences for the markers are as follows:
the primer sequences of ING1 are shown as SEQ ID NO.1 and SEQ ID NO.2;

the primer sequences of RAE1 are shown as SEQ ID NO.3 and SEQ ID NO.4;
the primer sequences of DOCK10 are shown as SEQ ID NO.5 and SEQ ID NO.6;
the primer sequences of KDSR are shown as SEQ ID NO.7 and SEQ ID NO.8;
the primer sequences of IVD are shown as SEQ ID NO.9 and SEQ ID NO.10; and
the primer sequences of MAEA are shown in SEQ ID NO.11 and SEQ ID NO.12.

Sources of the aforementioned markers for the diagnosis of myocardial infarction include, but are not limited to, blood, tissue fluid, urine, saliva, spinal fluid, and other body fluids from which genomic DNA may be obtained. In a specific embodiment of the present application, the source of the aforementioned markers for the diagnosis of myocardial infarction is blood.

The present application provides a method for the diagnosis of the tendency of incidence of myocardial infarction, which comprises the steps of: determining the expression level of myocardial infarction-related genes in a biological sample from a subject; the myocardial infarction-related genes are selected from the group consisting of ING1, RAE1, DOCK10, KDSR, IVD, and MAEA.

It indicates that the subject has or is at a risk of developing myocardial infarction if there is a significant increase in the expression level of at least one of ING1, RAE1, and MAEA, or a significant decrease in the expression level of at least one of DOCK10, KDSR, and IVD, in the biological sample from the subject, as compared to normal control levels.

Preferably, the method includes the steps of:
(1) collecting a biological sample from a subject;
(2) extracting RNA or protein in the biological sample from the subject, and determining the expression level of myocardial infarction-related genes; the myocardial infarction-related genes are selected from the group consisting of ING1, RAE1, DOCK10, KDSR, IVD, and MAEA;
(3) indicating that the subject has or is at a risk of developing myocardial infarction if there is a significant increase in the expression level of at least one of ING1, RAE1, and MAEA, or a significant decrease in the expression level of at least one of DOCK10, KDSR, and IVD, in the biological sample from the subject, as compared to normal control levels.

Furthermore, the method includes the steps of:
(1) identifying myocardial infarction-related genes as genes for the diagnosis of myocardial infarction; the myocardial infarction-related genes are selected from the group consisting of ING1, RAE1, DOCK10, KDSR, IVD, and MAEA;
(2) collecting a biological sample from a subject;
(3) extracting RNA or protein in the biological sample from the subject, and determining the expression level of myocardial infarction-related genes;
(4) indicating that the subject has or is at a risk of developing myocardial infarction if there is a significant increase in the expression level of at least one of ING1, RAE1, and MAEA, or a significant decrease in the expression level of at least one of DOCK10, KDSR, and IVD, in the biological sample from the subject, as compared to normal control levels.

Preferably, the biological sample is blood.

According to the present application, a gene expression level is considered to be "a significant increase" or "a significant decrease" when the expression level of the gene is increased or decreased by 10%, 25%, 50% compared to a normal control level. Alternatively, a gene expression level may be considered to be "a significant increase" or "a significant decrease" when expression of the gene is increased or decreased by at least 0.1 time, at least 0.2 time, at least 1 time, at least 2 times, at least 5 times, or at least 10 times or more as compared to a normal control level.

Methods for determining the expression level of myocardial infarction-related genes in a biological sample from a subject used in the present application include reverse transcription PCR, real-time quantitative PCR, immunoassay, in situ hybridization, chip detection, or high throughput sequencing platform sequencing.

In the context of the present application, "myocardial infarction-related gene" refers to a gene whose expression level in the blood of a patient with myocardial infarction is different from those in the blood of a normal control.

In the context of the present application, "normal control level" refers to the gene expression level detected in normal healthy individuals or individuals group who are known to have not suffered from myocardial infarction.

In the context of the present application, "normal control" refers to a normal healthy individual or individuals group who are known to have not suffered from myocardial infarction. Normal healthy individuals are individuals without clinical symptoms of myocardial infarction.

In the context of the present application, "ING1 gene" includes the polynucleotides of ING1 gene as well as any functional equivalents of ING1 gene. The sequence of ING1 gene (Chromosome 13, NC_000013.11 (110712623 . . . 110721074)) can be found in an international public nucleotide sequence database GeneBank.

In the context of the present application, "RAE1 gene" includes the polynucleotides of RAE1 gene as well as any functional equivalents of RAE1 gene. The sequence of RAE1 gene (Chromosome 20, NC_000020.11 (57351089 . . . 57378463)) can be found in an international public nucleotide sequence database GeneBank.

In the context of the present application, "DOCK10 gene" includes the polynucleotides of DOCK10 gene as well as any functional equivalents of the DOCK10 gene. The sequence of DOCK10 gene (Chromosome 2, NC_000002.12 (224765090 . . . 225042689, complement)) can be found in an international public nucleotide sequence database GeneBank.

In the context of the present application, "KDSR gene" includes polynucleotides of KDSR gene as well as any functional equivalents of KDSR gene. The sequence of KDSR gene (Chromosome 18, NC_000018.10 (63327736 . . . 63367273, complement)) can be found in an international public nucleotide sequence database GeneBank.

In the context of the present application, "IVD gene" includes polynucleotides of IVD gene as well as any functional equivalents of IVD gene. The sequence of IVD gene (Chromosome 15, NC_000015.10 (40405485 . . . 40435948)) can be found in an international public nucleotide sequence database GeneBank.

In the context of the present application, "MAEA gene" includes polynucleotides of MAEA gene as well as any functional equivalents of MAEA gene. The sequence of MAEA gene (Chromosome 4, NC_000004.12 (1289851 . . . 1340148)) can be found in an international public nucleotide sequence database GeneBank.

In the context of the present application, gene expression products include a protein encoded by the gene and partial peptides of the protein encoded by the gene. The partial peptides of the protein contain functional domains associated with myocardial infarction.

"Protein" includes proteins and any functional equivalents thereof. Such functional equivalents include protein conservatively variant proteins, or active fragments thereof, or active derivatives thereof, allelic variants, natural mutants, inducible mutants, and proteins encoded by DNA capable of hybridizing to DNA under high or low stringency conditions.

In general, it is known that modification of one or more amino acids in a protein does not affect the function of the protein. Those skilled in the art will recognize that changes to a single amino acid or a small percentage of amino acids or individual additions, deletions, insertions, substitutions to an amino acid sequence are conservative modifications in which the changes in a protein result in a protein having a similar function. Conservative substitution tables that provide functionally similar amino acids are well known in the art.

An example of a protein modified by the addition of one or more amino acid residues is a fusion protein of the aforementioned markers. There is no limitation on the peptide or protein to which the protein is fused, so long as the resulting fusion protein retains the biological activity of the marker.

In the context of the present application, "diagnosis of myocardial infarction" includes both determining whether the subject has suffered from myocardial infarction and determining whether the subject is at a risk of suffering from myocardial infarction.

The advantages and beneficial effects of the present application are as follows:

The present application discovered for the first time that ING1, RAE1, DOCK10, KDSR, IVD, and MAEA gene expression are associated with myocardial infarction. By detecting the expression of ING1, RAE1, DOCK10, KDSR, IVD, and MAEA in the subject, it can be determined whether the subject is suffering from myocardial infarction, or determine whether the subject is at a risk of suffering from a myocardial infarction, so as to guide the clinician to provide the subject with a prevention plan or treatment plan.

The present application has discovered a new molecular marker including ING1, RAE1, DOCK10, KDSR, IVD, and MAEA. Compared with traditional detection methods, molecular diagnosis is more timely, specific and sensitive, and can realize the early diagnosis of myocardial infarction, thereby reducing the mortality of myocardial infarction.

DETAILED DESCRIPTION OF THE INVENTION

The present application is further described in detail below with reference to the accompanying drawings and examples. The following examples are only intended to illustrate the present application, rather than limiting the scope of the present application The experimental methods without specific conditions in the examples usually follow conventional conditions, such as those described in Sambrook et al., Molecular Cloning: Laboratory Manual (New York: Cold Spring Harbor Laboratory Press, 1989), or the conditions recommended by the manufacturer.

Example 1 Screening of Genes of Differential Expression in Patients with Myocardial Infarction and Normal Subjects 1. Objects of Study Six hospitalized patients with myocardial infarction treated in hospital were selected as the study objects, including 3 males and 3 females, with an average age of 56.00±8.75; the control group consisted of 7 healthy people; each of the above patients and healthy people who were invited to join the study signed an informed consent form.

2. Collection and Storage of Samples

On the day of admission, 8 mL of fresh sterile arterial blood was collected into EDTA anticoagulated purple-headed tubes before coronary angiography. If it is not used immediately, the sample could be stored in a refrigerator at 4° C. for 2 h.

3. Isolation of PBMCs by a Ficoll Method

The following steps were all completed in an ultra-clean bench:

(1) The blood sample was diluted with an equal volume of normal saline, an equal volume of Ficoll solution (human lymphocyte separation solution, purchased from Tianjin Haoyang Biological Product Technology Co., Ltd.) was added into a 50 mL centrifuge tube, the centrifuge tube was tilted at an angle of 45° C., the diluted blood sample was pipetted with an RNase-free pipette tip and slowly added above the separation liquid level along the tube wall, so that the blood sample was spread on the Ficoll separation liquid to ensure the integrity of liquid layer; the tube cap was tighten.

(2) The tubes were placed in a horizontal centrifuge, and centrifuged at 800 g for 20 min at room temperature, with the speed increasing slowly.

(3) The serum layer was pipetted and discarded, the PBMCs-rich buffy coat cells were pipetted from the interface of serum layer and separation solution along the tube wall with an RNase-free pipette tip and placed in a new 10 mL RNase-free EP tube, normal saline was added to 10 mL, followed by blending well, and centrifuging at 1700 r/min for 15 min at room temperature.

(4) The supernatant was discarded and the sediment at the bottom of the tube was PBMCs, then 1 mL of normal saline was added into the tube, the sediment was blended evenly by pipetting and then transferred to a 1.5 mL RNase-free EP tube, followed by centrifuging at 1500 r/min for 10 min at room temperature, and the cells were washed again.

(5) The supernatant was discarded and 1 mL Trizol was added to blend evenly by pipetting. If RNA was not immediately extracted, it could be stored in a refrigerator at −80° C. refrigerator for 2 h.

4. Extraction of RNA from PBMCs

Total RNA was extracted by one-step phenol-chloroform method. All steps were performed on ice, requiring RNase-free masks and gloves. The steps were as follows:

(1) PBMCs dissolved in Trizol were taken from the −80° C. refrigerator and slowly dissolved.

(2) To each tube was added 200 μl of trichloromethane, followed by vigorous shaking for 15 sec and centrifuging at 12000 r/min for 15 min at 4° C.

(3) The upper liquid phase was pipetted (without touching the middle layer and the lower layer) in a newly prepared 1.5 mL enzyme-free EP tube, 500 μl of isopropyl alcohol was added in equal volume, followed by inversion and blending uniformly, standing for 10 min at room temperature, and centrifuging at 12000 r/min for 15 min at 4° C.

(4) The supernatant was discarded, 1 mL of 75% ethanol (prepared DEPC in water) was added, followed by blending uniformly several times by inversion, the sediment was washed and then centrifuged at 7500 r/min for 10 min at 4° C.

(5) The supernatant was discarded, the liquid in the tube was pipetted as far as possible on the premise of not touching the sediment, followed by standing open in the ultra-clean bench for 15-20 min, after drying the sediment, and 15-20 μl/1000 RNase-free water was added to dissolve RNA.

(6) Detection of RNA purity: 2 μL dissolved RNA sample was added in a detected self-inspected and zeroed microplate reader for direct acquisition of RNA concentration. OD260/OD280 at 1.8-2.2 indicated that the extracted RNA was highly pure for later use.

5. High Throughput Transcriptome Sequencing (1) RNA-Seq Reads Mapping

Firstly the low-quality reads were removed to get clean reads, and then the clean reads were matched with the UCSC *H. sapiens* reference genome (hg19) using TopHat v1.3.1, wherein the pre-built index of *H. sapiens* UCSC hg19 version was downloaded from the TopHat homepage as a reference genome. When TopHat was used for genome matching, each read (default to 20) was allowed to have multiple matching sites, up to 2 mismatches. A possible splicing sites library was built by TopHat based on exon regions and GT-AG cleavage signals, and reads that were not mapped to the genome were mapped to the genome according to the splicing sites library. The system default parameters of the TopHat method were used.

(2) Assessment of Transcript Abundance

The matched reads files were treated with Cufflinks v1.0.3, which normalized the number of RNA-seq fragments to calculate the relative abundance of transcripts. The FPKM value referred to the number of fragments per million sequenced fragments matched to the 1 kb exon region of a specific gene. The confidence interval of the FPKM estimation value was calculated through a Bayesian inference method. The referenced GTF annotation files used by Cufflinks were downloaded from the Ensembl database (*Homo_sapiens*. GRCh37.63.gtf).

(3) Detection of Differentially Expressed Genes

The downloaded Ensembl GTF files and the original files matched through TopHat were transmitted to Cuffdiff which re-estimated the expression abundance of transcripts listed in the GTF files by using the original matched files and detected differential expression. In the Cuffidff output, only the q value which was <0.01 was considered as a differential expression.

6. Results

The RNA-seq results showed that compared with the normal population, there were 347 highly-expressed genes and 254 low-expressed genes in the blood of patients with myocardial infarction, with the difference being statistically significant ($P<0.05$).

Example 2 Verification of Differentially Expressed Genes in Patients with Myocardial Infarction and Normal Subjects by a QPCR Assay 1. Objects of Study The screening criteria were the same as in Example 1, including 35 patients with myocardial infarction and 35 normal subjects.

2. Extraction of Total RNA

The steps were the same as Example 1.

3. RT-PCR (1) RT

RT Reaction System (20 μl):

| | |
|---|---|
| Anchored Oligo(dT)18 (0.5 μg/μL) | 1 μL |
| 2XTS Reaction Mix | 10 μL |
| TransScript ® RT/RI Enzyme Mix | 1 μL |
| Total RNA | 75 ng |
| RNase-free Water | to 20 μL |

RT Reaction Procedure:

| | |
|---|---|
| 42° C. | 15 min |
| 85° C. | 5 s |
| 4° C. | — |

(2) qPCR

PCR Reaction System (20 μl):

| | |
|---|---|
| Master Mix, 2* conc | 9 μl |
| Forward Primer (4 μM) | 1 μl |
| Reverse Primer (4 μM) | 1 μl |
| cDNA Template | 1 μl |
| Water, PCR grade | 8 μl |

PCR Reaction Procedure:
ING1 Amplification Procedure:
Stage 1 95° C. 10 min
Stage 2 95° C. 10 s
51° C. 10 s
Repeating 45 cycles
RAE1 Amplification Procedure:
Stage 1 95° C. 10 min
Stage 2 95° C. 10 s
56° C. 10 s
Repeating 35 cycles DOCK10 Amplification Procedure:
Stage 1 95° C. 10 min
Stage 2 95° C. 10 s
55° C. 10 s
Repeating 40 cycles
KDSR Amplification Procedure:
Stage 1 95° C. 10 min
Stage 2 95° C. 10 s
60° C. 10 s
Repeating 40 cycles;
IVD Amplification Procedure:
Stage 1 95° C. 10 min
Stage 2 95° C. 10 s
57° C. 10 s
Repeating 42 cycles
MAEA Gene Amplification Procedure:
Stage 1 95° C. 10 min
Stage 2 95° C. 10 s
51° C. 10 s
Repeating 45 cycles
3 replicate wells were set up for each sample, with internal reference as GAPDH.
(3) Primers
The sequences of respective primers were as follows:

```
ING1 gene:
Forward primer:
                                        (SEQ ID NO. 1)
5'-CAAGGAACCTCAAGTCAT-3';

Reverse primer:
                                        (SEQ ID NO. 2)
5'-CTCACATACAGCAGGAAG-3'.

RAE1 gene:
Forward primer:
                                        (SEQ ID NO. 3)
5'-CAACTACAGACAATCACAATCC-3';

Reverse primer:
                                        (SEQ ID NO. 4)
5'-AAGACAGACAACCAATGCTA-3'.

DOCK10 gene:
Forward primer:
                                        (SEQ ID NO. 5)
5'-GTCTGGATTCGCTGGATAA-3';

Reverse primer:
                                        (SEQ ID NO. 6)
5'-CGTGTAGGTTGTTCTCTGA-3'.

KDSR gene:
Forward primer:
                                        (SEQ ID NO. 7)
5'-GACTATAACCAAGTAGAGAA-3';

Reverse primer:
                                        (SEQ ID NO. 8)
5'-TTGATGCTCATTAACCTT-3'.

IVD gene:
Forward primer:
                                        (SEQ ID NO. 9)
5'-GCTCTGATGTTGTCTCTATGAA-3';

Reverse primer:
                                        (SEQ ID NO. 10)
5'-ATCCAGAACTTGTTGCCATT-3'.

MAEA gene:
Forward primer:
                                        (SEQ ID NO. 11)
5'-GTGATGAACGAGAACAAT-3';

Reverse primer:
                                        (SEQ ID NO. 12)
5'-GGATAGAAAGCAGAGAATT-3'.

GAPDH gene:
Forward primer:
                                        (SEQ ID NO. 13)
5'-CCACATCGCTCAGACACCAT-3';

Reverse primer:
                                        (SEQ ID NO. 14)
5'-GGCAACAATATCCACTTTACCAGAGT-3'.
```

4. Results and Analysis

The Ct value was the corresponding cycle number when the fluorescence intensity in the tube reaches the exponential growth stage from the background.

The formula was as follows: sample Ct value-internal reference (GAPDH) Ct value=$\Delta$Ct; sample $\Delta$Ct value-Negative control $\Delta$Ct=$\Delta\Delta$Ct; sample mRNA relative value= $2^{-\Delta\Delta Ct}$.

(5) Data Statistics

All data were shown as mean±standard deviation (Mean±SD). Variance analysis was performed on the differences between multiple sets of data $P<0.05$ was considered statistically significant.

4. Results

Figure 1:
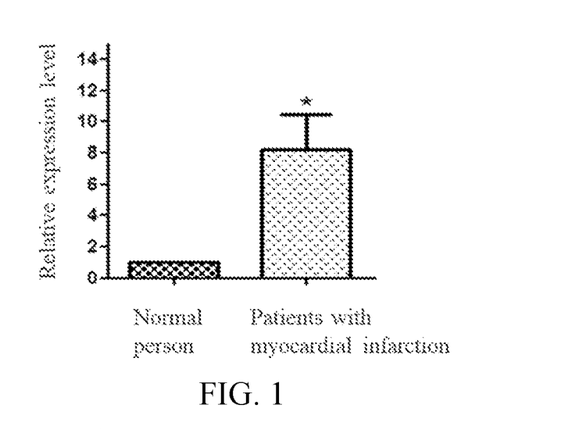
FIG. 1 shows the difference in the expression of ING1 gene in patients with myocardial infarction and normal subjects detected by using QPCR.

The results showed that there was a significant increase in mRNA level of ING1 gene in 32 of 35 patients with myocardial infarction compared with the average level of normal subjects. Statistical results were shown in FIG. 1, compared with normal subjects, there was a significant increase in mRNA level of ING1 gene in the blood of patients with myocardial infarction, with the difference being statistically significant ($P<0.05$). The results were the same as that of RNA-seq assay.

Figure 2:
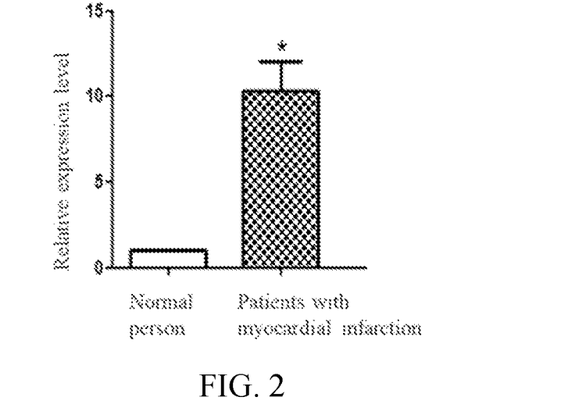
FIG. 2 shows the difference in the expression of RAE1 gene in patients with myocardial infarction and normal subjects detected by using QPCR.

The results showed that there was a significant increase in mRNA level of RAE1 gene in 32 of 35 patients with myocardial infarction compared with the average level of normal subjects. Statistical results were shown in FIG. 2, compared with normal subjects, there was a significant increase in mRNA level of RAE1 gene in the blood of patients with myocardial infarction, with the difference being statistically significant ($P<0.05$). The results were the same as that of RNA-seq assay.

Figure 3:
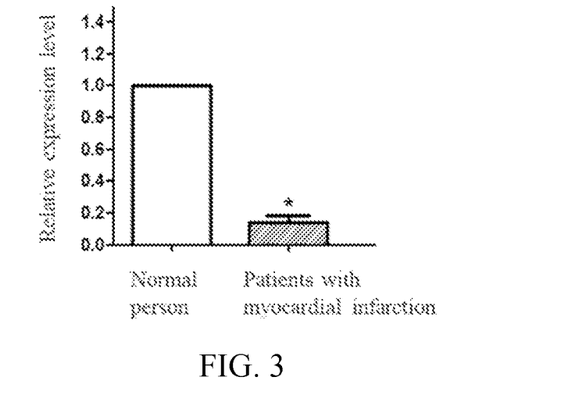
FIG. 3 shows the difference in the expression of DOCK10 gene in patients with myocardial infarction and normal subjects detected by using QPCR.

The results showed that there was a significant decrease in mRNA level of DOCK10 gene in 33 of 35 patients with myocardial infarction compared with the average level of normal subjects. Statistical results were shown in FIG. 3, compared with normal subjects, there was a significant decrease in mRNA level of DOCK10 gene in the blood of patients with myocardial infarction, with the difference being statistically significant ($P<0.05$). The results were the same as that of RNA-seq assay.

Figure 4:
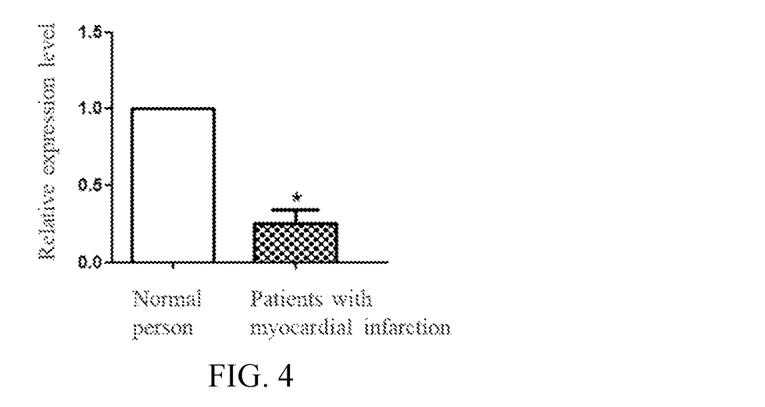
FIG. 4 shows the difference in the expression of KDSR gene in patients with myocardial infarction and normal subjects detected by using QPCR.

The results showed that there was a significant decrease in mRNA level of KDSR gene in 30 of 35 patients with myocardial infarction compared with the average level of normal subjects. Statistical results were shown in FIG. 4, compared with normal subjects, there was a significant decrease in mRNA level of KDSR gene in the blood of patients with myocardial infarction, with the difference being statistically significant ($P<0.05$). The results were the same as that of RNA-seq assay.

Figure 5:
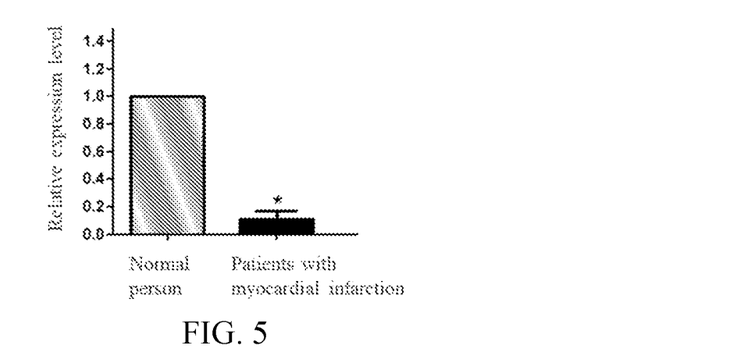
FIG. 5 shows the difference in the expression of IVD gene in patients with myocardial infarction and normal subjects detected by using QPCR.

The results showed that there was a significant decrease in mRNA level of IVD in 34 of 35 patients with myocardial infarction compared with the average level of normal subjects. Results were shown in FIG. 5, compared with normal subjects, there was a significant decrease in mRNA level of IVD gene in the blood of patients with myocardial infarction, with the difference being statistically significant (P<0.05). The results were the same as that of RNA-seq assay.

Figure 6:
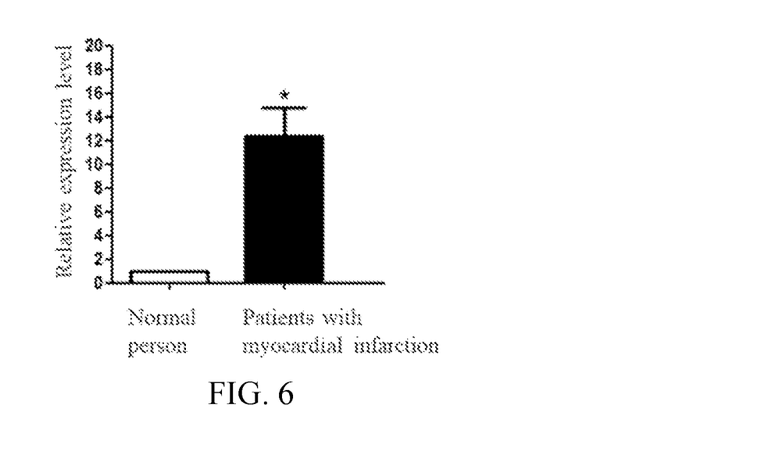
FIG. 6 shows the difference in the expression of MAEA gene in patients with myocardial infarction and normal subjects detected by using QPCR.

The results showed that there was a significant increase in mRNA level of MAEA gene in 34 of 35 patients with myocardial infarction compared with the average level of normal subjects. Statistical results were shown in FIG. 6, compared with normal subjects, there was a significant increase in mRNA level of MAEA gene in the blood of patients with myocardial infarction, with the difference being statistically significant (P<0.05). The results were the same as that of RNA-seq assay.

Example 3 Verification of the Expression Products of Differentially Expressed Genes in Patients with Myocardial Infarction and Normal Subjects by an Immunoblotting Assay 1. Objects of study: the same as Example 2.
2. Separation of Monocytes 10 ml of venous blood of was collected from patients with myocardial infarction and normal subjects and injected into sterile heparin-containing vials, which were gently shaken immediately after capping. An equal volume of HBSS (NaCl 8.0 g, $Na_2HPO_4$ 0.132 g, $KH_2PO_4$ 0.06 g, KCl 0.4 g, phenol red 1 ml, $NaHCO_3$ 0.35 g, and D-glucose 1.0 g, dissolving in 1000 ml of double distilled water) was added with a sterile pipette to reduce aggregation of red blood cells. 8 ml lymphocyte stratification solution was pipetted into a 50 ml centrifuge tube, the diluted blood was slowly added along the wall of the tube, keeping the interface clear without blending the two, centrifugation was performed at 2000 r/min for 30 min at 20° C., the turbid off-white layer was pipetted carefully at the interface of the stratification solution and plasma, i.e. the lymphocyte layer, and added to another centrifuge tube, followed by washing twice with 5 volumes of HBSS, and centrifuging at 2000 r/min and 1500 r/min in turn for 10 min at room temperature to remove most of the blended platelets, the remaining cell mass was blended with 10 ml of double distilled water for 1 min to lyse the residual red blood cells, then an equal amount of 1.8% NaCl solution was rapidly added, the mixture was centrifuged at 2000 r/min, the supernatant was removed, and the cells were counted and adjusted to $1 \times 10^6$ cells/ml with HBSS solution for later use.

3. Extraction of Total Protein of Monocytes

The cell suspension (with a concentration of $1 \times 10^6$ cells/ml) obtained in the assay was centrifuged at 1000 r/min for 10 min at room temperature, the supernatant was discarded, 100 μl lysis buffer solution was added, followed by oscillating for 1 h at 4° C., crushing the cells by an ultrasonic instrument for 10 s each time for 10 times, and centrifuging at 12,000 r/min for 1 h at 4° C.; the supernatant was quantified by a Brandford method and subpackaged into 2.5 μg/μl, and stored at a −80° C. refrigerator for later use.

4. Western Blotting Assay

It was performed by conventional methods.

5. Statistical Treatment The gray value of the protein strip was analyzed by using Image J software, and the gray value of the target white strip was normalized taking β-actin as an internal reference. Results Data were expressed as mean±standard deviation. SPSS13.0 statistical software was used for statistical analysis. A t-test was used to determine if there was a significant difference between the two groups. P<0.05 was considered statistically significant.

6. Results

Figure 7:
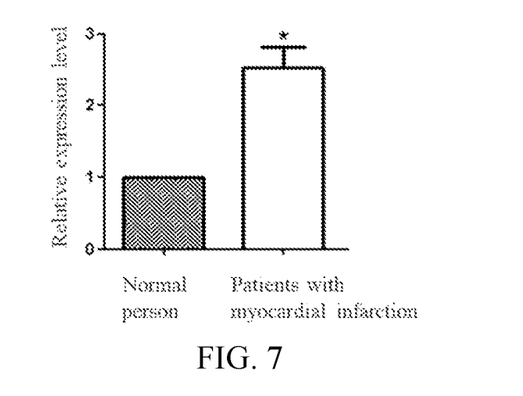
FIG. 7 shows the difference in the expression of ING1 protein in patients with myocardial infarction and normal subjects detected by using immunoblotting.

The results showed that there was a significant increase in the level of ING1 protein in 32 of 35 patients with myocardial infarction compared with the average level of normal subjects. Statistical results as shown in FIG. 7, compared with normal subjects, there was a significant increase in the level of ING1 protein in the blood of patients with myocardial infarction, with the difference being statistically significant (P<0.05).

Figure 8:
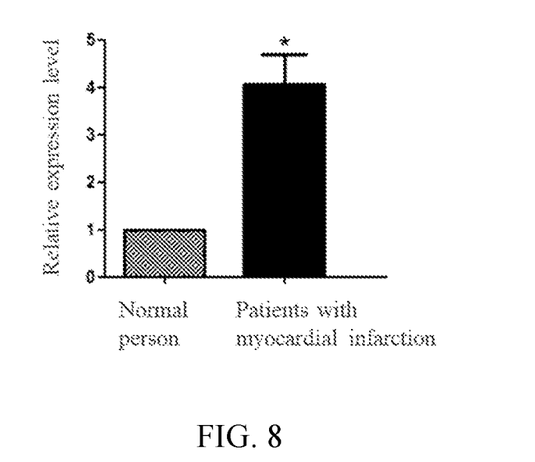
FIG. 8 shows a graph of the difference in the expression of RAE1 protein in patients with myocardial infarction and normal subjects detected by using immunoblotting.

The results showed that there was a significant increase in the level of RAE1 protein in 32 of 35 patients with myocardial infarction compared with the average level of normal subjects. Statistical results As shown in FIG. 8, compared with normal subjects, there was a significant increase in the level of RAE1 protein in the blood of patients with myocardial infarction, with the difference being statistically significant (P<0.05).

Figure 9:
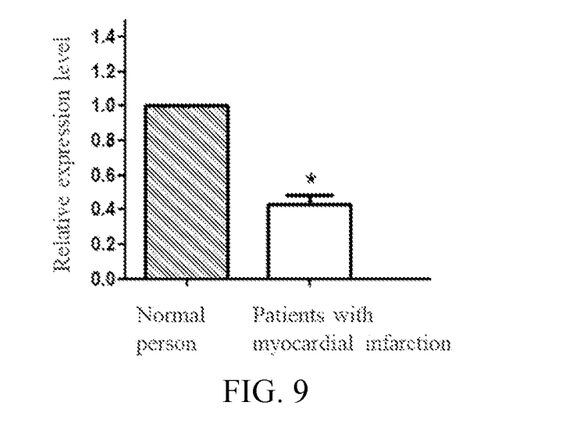
FIG. 9 shows the difference in the expression of DOCK10 protein in patients with myocardial infarction and normal subjects detected by using immunoblotting.

The results showed that there was a significant decrease in the level of DOCK10 protein in 33 of 35 patients with myocardial infarction compared with the average level of normal subjects. Statistical results as shown in FIG. 9, compared with normal subjects, there was a significant decrease in the level of DOCK10 protein in the blood of patients with myocardial infarction, with the difference being statistically significant (P<0.05).

Figure 10:
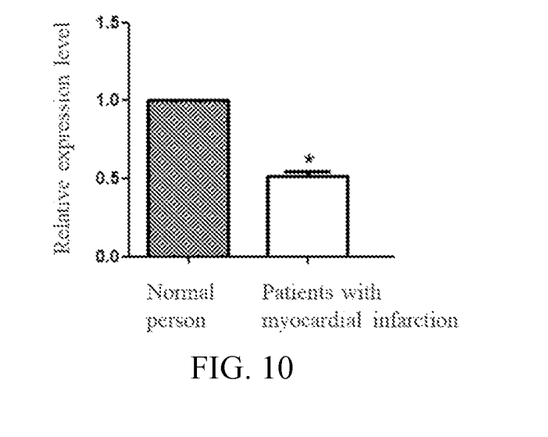
FIG. 10 shows the difference in the expression of KDSR protein in patients with myocardial infarction and normal subjects detected by using immunoblotting.

The results showed that there was a significant decrease in the level of KDSR protein in 30 of 35 patients with myocardial infarction compared with the average level of normal subjects. Statistical results as shown in FIG. 10, compared with normal subjects, there was a significant decrease in the level of KDSR protein in the blood of patients with myocardial infarction, with the difference being statistically significant (P<0.05).

Figure 11:
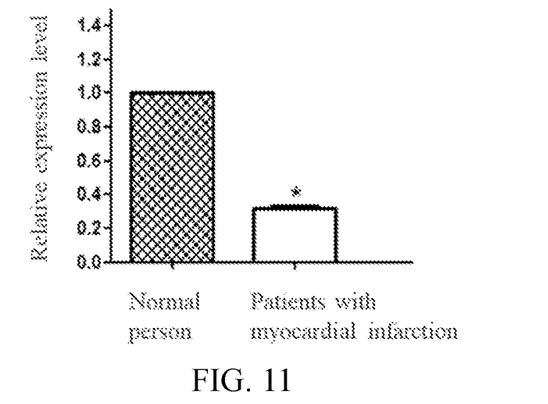
FIG. 11 shows the difference in the expression of IVD protein in patients with myocardial infarction and normal subjects detected by using immunoblotting.

The results showed that there was a significant decrease in the level of IVD protein in 34 of 35 patients with myocardial infarction compared with the average level of normal subjects. Statistical results as shown in FIG. 11, compared with normal subjects, there was a significant decrease in the level of IVD protein in the blood of patients with myocardial infarction, with the difference being statistically significant (P<0.05).

Figure 12:
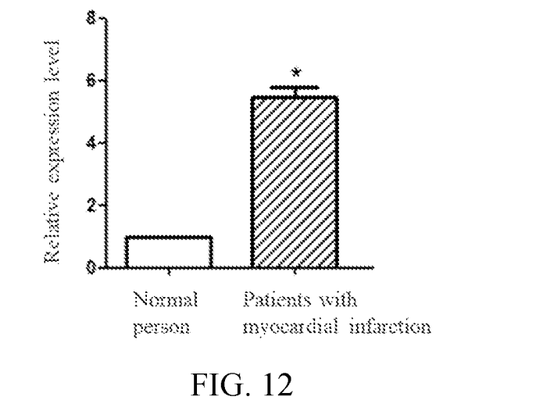
FIG. 12 shows the difference in the expression of MAEA protein in patients with myocardial infarction and normal subjects detected by using immunoblotting.

The results showed that there was a significant increase in the mRNA level of MAEA protein in 34 of 35 patients with myocardial infarction compared with the average level of normal subjects. Statistical results as shown in FIG. 12, compared with normal subjects, there was a significant increase in the level of MAEA protein in the blood of patients with myocardial infarction, with the difference being statistically significant (P<0.05).

The description of the above Examples is only used to understand the method and core idea of the present application. It should be noted that, several improvements and modifications may be made by those of ordinary skill in the art without departing from the principle of the present application, and these improvements and modifications should also be considered within the protection scope of the present invention.

The invention claimed is:

1. A method for analyzing a myocardial infarction-related gene, comprising the steps of:
   (i) determining the expression level of a myocardial infarction-related gene in a biological sample from a subject, wherein the myocardial infarction-related gene is RAE1 and the biological sample is monocytes in the blood; and
   (ii) comparing the expression level of RAE1 from step (i) to a normal control level of RAE1 in monocytes from a human that has not had MI,
wherein:
   determining the expression level of a myocardial infarction-related gene in a biological sample from a subject comprises amplifying a fragment of an RAE1 transcript in the biological sample with the primers SEQ ID NO: 3 and SEQ ID NO: 4 and determining the expression level of RAE1 using chip detection or high throughput sequencing;
   an increase in the expression level of RAE1 in the sample from the subject compared to the normal control level indicates that the subject has myocardial infarction; and the subject is human.

2. The method according to claim 1, wherein the determining the expression level of a myocardial infarction-related gene in a biological sample from a subject further comprises collecting the biological sample from the subject.

3. The method according to claim 1, wherein the expression level in the sample from the subject is increased by at least 10% compared to the normal control level.

* * * * *

SEQUENCE LISTING

<160> NUMBER OF SEQ ID NOS: 14

<210> SEQ ID NO 1
<211> LENGTH: 18
<212> TYPE: DNA
<213> ORGANISM: Artificial Sequence
<220> FEATURE:
<223> OTHER INFORMATION: forward primer for ING1 gene

<400> SEQUENCE: 1
caaggaacct caagtcat                                                    18

<210> SEQ ID NO 2
<211> LENGTH: 18
<212> TYPE: DNA
<213> ORGANISM: Artificial Sequence
<220> FEATURE:
<223> OTHER INFORMATION: reverse primer for ING1 gene

<400> SEQUENCE: 2
ctcacataca gcaggaag                                                    18

<210> SEQ ID NO 3
<211> LENGTH: 22
<212> TYPE: DNA
<213> ORGANISM: Artificial Sequence
<220> FEATURE:
<223> OTHER INFORMATION: forward primer for RAE1 gene

<400> SEQUENCE: 3
caactacaga caatcacaat cc                                               22

<210> SEQ ID NO 4
<211> LENGTH: 20
<212> TYPE: DNA
<213> ORGANISM: Artificial Sequence
<220> FEATURE:
<223> OTHER INFORMATION: reverse primer for RAE1 gene

<400> SEQUENCE: 4
aagacagaca accaatgcta                                                  20

<210> SEQ ID NO 5
<211> LENGTH: 19
<212> TYPE: DNA
<213> ORGANISM: Artificial Sequence
<220> FEATURE:
<223> OTHER INFORMATION: forward primer for DOCK10 gene

<400> SEQUENCE: 5
gtctggattc gctggataa                                                   19

<210> SEQ ID NO 6
<211> LENGTH: 19
<212> TYPE: DNA
<213> ORGANISM: Artificial Sequence
<220> FEATURE:
<223> OTHER INFORMATION: reverse primer for DOCK10 gene

<400> SEQUENCE: 6
cgtgtaggtt gttctctga                                                   19

<210> SEQ ID NO 7
<211> LENGTH: 20
<212> TYPE: DNA
<213> ORGANISM: Artificial Sequence

```
<220> FEATURE:
<223> OTHER INFORMATION: forward primer for KDSR gene

<400> SEQUENCE: 7
gactataacc aagtagagaa                                                   20

<210> SEQ ID NO 8
<211> LENGTH: 18
<212> TYPE: DNA
<213> ORGANISM: Artificial Sequence
<220> FEATURE:
<223> OTHER INFORMATION: reverse primer for KDSR gene

<400> SEQUENCE: 8
ttgatgctca ttaacctt                                                     18

<210> SEQ ID NO 9
<211> LENGTH: 22
<212> TYPE: DNA
<213> ORGANISM: Artificial Sequence
<220> FEATURE:
<223> OTHER INFORMATION: forward primer for IVD gene

<400> SEQUENCE: 9
gctctgatgt tgtctctatg aa                                                22

<210> SEQ ID NO 10
<211> LENGTH: 20
<212> TYPE: DNA
<213> ORGANISM: Artificial Sequence
<220> FEATURE:
<223> OTHER INFORMATION: reverse primer for IVD gene

<400> SEQUENCE: 10
atccagaact tgttgccatt                                                   20

<210> SEQ ID NO 11
<211> LENGTH: 18
<212> TYPE: DNA
<213> ORGANISM: Artificial Sequence
<220> FEATURE:
<223> OTHER INFORMATION: forward primer for MAEA gene

<400> SEQUENCE: 11
gtgatgaacg agaacaat                                                     18

<210> SEQ ID NO 12
<211> LENGTH: 19
<212> TYPE: DNA
<213> ORGANISM: Artificial Sequence
<220> FEATURE:
<223> OTHER INFORMATION: reverse primer for MAEA gene

<400> SEQUENCE: 12
ggatagaaag cagagaatt                                                    19

<210> SEQ ID NO 13
<211> LENGTH: 20
<212> TYPE: DNA
<213> ORGANISM: Artificial Sequence
<220> FEATURE:
<223> OTHER INFORMATION: forward primer for GAPDH gene

<400> SEQUENCE: 13
ccacatcgct cagacaccat                                                   20
```

```
<210> SEQ ID NO 14
<211> LENGTH: 26
<212> TYPE: DNA
<213> ORGANISM: Artificial Sequence
<220> FEATURE:
<223> OTHER INFORMATION: reverse primer for GAPDH gene

<400> SEQUENCE: 14
ggcaacaata tccactttac cagagt                                          26
```